United States Patent [19]

Ashley

[11] 4,313,440
[45] Feb. 2, 1982

[54] MULTIPURPOSE DOUBLE BARREL SYRINGE AND METHOD OF MANUFACTURE OF SAME

[76] Inventor: Sheldon J. Ashley, 147-15 84th Rd., Jamaica, N.Y. 11435

[21] Appl. No.: 190,620

[22] Filed: Sep. 8, 1980

[51] Int. Cl.³ .............................................. A61M 5/00
[52] U.S. Cl. ............................ 128/218 R; 128/218 N
[58] Field of Search .................. 128/213, 215, 218 R, 128/218 N, 218 M, 218 D, 220, 221, 762, 272.1, 272.3

[56] References Cited

U.S. PATENT DOCUMENTS

| | | | |
|---|---|---|---|
| 3,621,843 | 11/1971 | Metten | 128/221 |
| 3,749,084 | 7/1973 | Cucchiara | 128/218 N X |
| 3,911,916 | 10/1975 | Stevens | 128/218 R |
| 4,036,225 | 7/1977 | Maury | 128/218 M |
| 4,055,177 | 10/1977 | Cohen | 128/218 M |
| 4,188,949 | 2/1980 | Antoshkiw | 128/218 M |

Primary Examiner—John D. Yasko
Attorney, Agent, or Firm—Daniel Jay Tick

[57] ABSTRACT

A multipurpose double barrel syringe is manufactured by disassembling a first syringe having a first predetermined capacity, a first cylinder, a first hypodermic needle of a first gauge at a first end thereof, a first piston plunger having a plunger tip with a smooth seating surface and a rear indentation and a first collar extending radially therefrom at a spaced opposite second end thereof, and a second syringe having a second cylinder with a second predetermined capacity less than the first predetermined capacity, the second cylinder having a second collar extending substantially radially therefrom at a first end thereof, a second needle of a second gauge with a tip and a base and a second piston plunger having a piston rod having a second plunger tip coaxially mounted at a first end thereof coaxially slidably mounted in the second cylinder for movement in axial directions and a third collar extending radially therefrom at a spaced opposite second end thereof. The first needle is retained on the first cylinder and the second piston plunger is retained in the second cylinder. The second needle is inserted through the center of the plunger tip of the first piston plunger. The second needle is cemented in the plunger tip of the first piston plunger. The second needle and plunger tip are mounted on the second cylinder to provide a second syringe assembly. The second syringe assembly is inserted in the first cylinder in a manner whereby the second syringe assembly functions as a second syringe and as a piston plunger assembly of the first cylinder. A spacer member is positioned to extend between the second and third collars to prevent the second piston plunger from moving into the second cylinder except under manual pressure.

14 Claims, 12 Drawing Figures

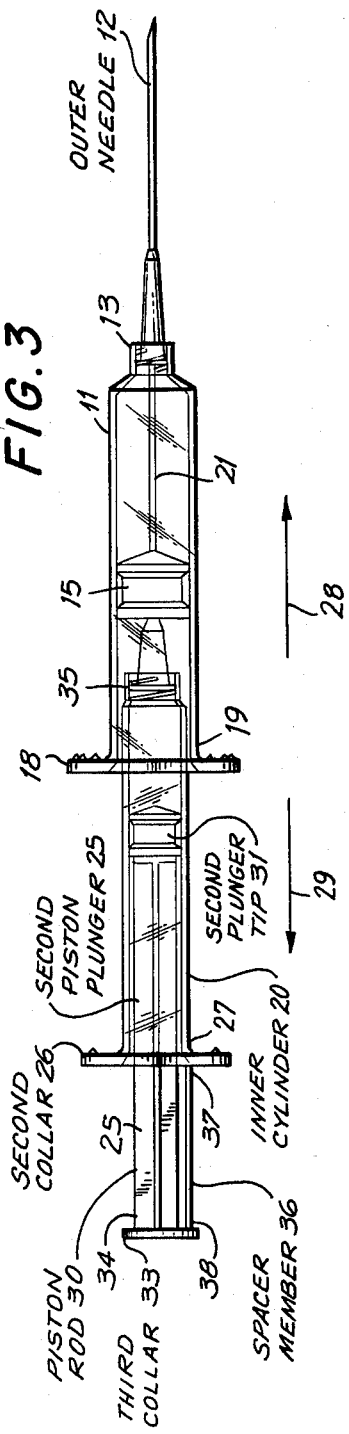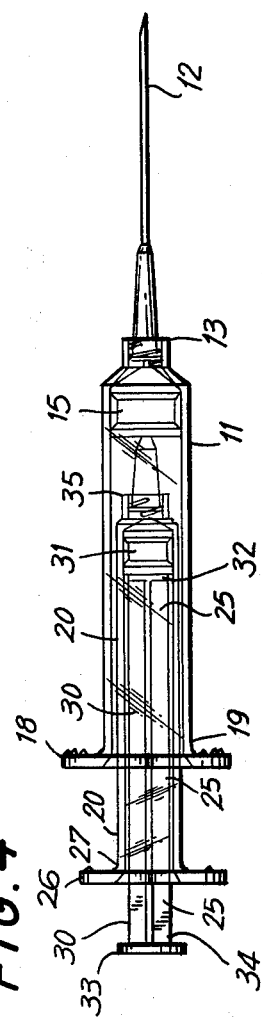

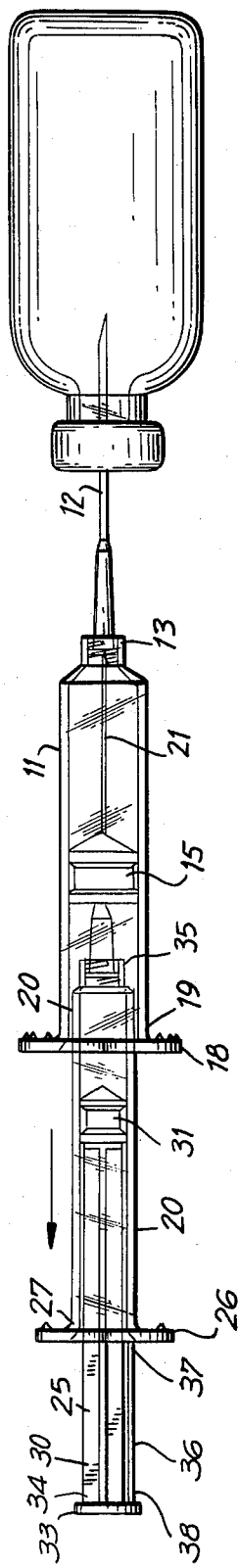
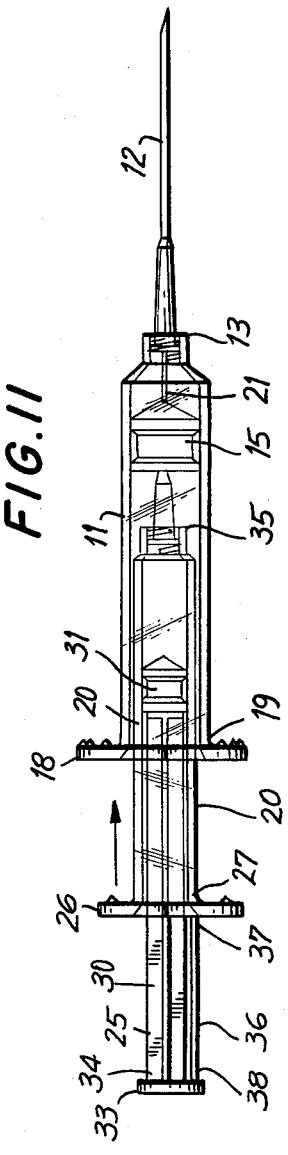
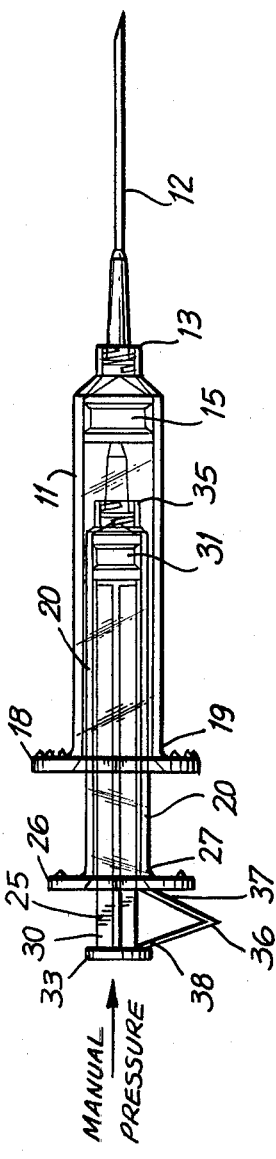

MULTIPURPOSE DOUBLE BARREL SYRINGE AND METHOD OF MANUFACTURE OF SAME

BACKGROUND OF THE INVENTION

The present invention relates to a multipurpose double barrel syringe. More particularly, the invention relates to a multipurpose double barrel syringe and a method of manufacture of same.

Venipuncture, along with the intravenous administration of radiopharmaceuticals, is an intricate part of a nuclear medicine technologist's profession. Whether injections are made promptly by an experienced technologist or throughout the day by attending and house staff physicians, expedient technique is a necessity. There are negative and positive pressures exerted between the first, or outer, cylinder of a first, or outer, syringe, and the second, or inner, cylinder of a second, or inner, syringe. This causes the opposite cylinder to draw in material or discharge its contents at the wrong time.

When the outer cylinder of a known double barrel syringe is loaded through its needle, a negative pressure is created which tends to draw the contents of the inner cylinder into the outer cylinder or vial used to fill the outer cylinder. Furthermore, when the needle is used in a vein, there is a negative pressure, or suction, exerted by the blood passing in the vein. This has a sucking or drawing effect on the needle of the inner cylinder and the subsequent contents of the inner cylinder which causes a discharge of the inner cylinder without manual pressure being applied to its piston plunger. Once the first needle is in the vein, when the piston plunger of the outer cylinder is manually drawn back, as required, this effect of unintended discharge of the inner cylinder is greatly magnified. Also, when the contents of the outer cylinder are discharged, a positive pressure effect is created due to the resistance against the discharge. This causes a backup of the contents of the outer cylinder, which are trying to be discharged into the inner cylinder, which has not yet been discharged.

An injectable material is frequently required to be followed by a flushing material, other than in just nuclear medicine, in X-ray procedures, where dyes are rapidly injected and pictures taken, as in angiography.

Frequently, dual injections are required, but the two drug contents of the two cylinders cannot be mixed prior to administration.

Whenever an antagonistic test is performed, wherein a strong drug is administered to bring on an attack or reaction in a patient for diagnosis of disease, the antidote or neutralizing agent or drug must be administered immediately.

It may be necessary to have an intravenous drug immediately available for a critically ill patient.

Sometimes, the use of two syringes is indicated in a situation where a two or three way stopcock would be indicated.

It is often necessary to purposely mix and/or incubate a material with the blood of a patient. The mixture is then reinjected into the patient such as, for example, in vitro labeling of red blood cells with $Tc^{99m}$.

A wet/dry syringe may be required for mixing prepackaged materials.

Known intravenous delivery systems include a common hypodermic syringe and needle, starting a normal saline intravenous drip, maneuvering a three-way stopcock and using a butterfly infusion set. When a common hypodermic syringe and needle is used, a residual amount of radionuclide is left in the syringe, blood may mix in the syringe when introducing lung imaging material, more than one venipuncture is necessary in dual radionuclide studies, and no bolus or bolus flush is available without time delay in flow studies. Starting a normal saline intravenous solution is cumbersome for one person and time consuming. The positive force of injection may cause the needle to pop out of the skin or tubing to disconnect from the intravenous set when using a butterfly infusion set. No bolus or bolus flush is available without time delay in flow studies. Maneuvering a three-way stopcock leaves a residual amount of radionuclide in the syringe, is cumbersome for one person, time consuming, and the positive force of injection may cause the needle to pop out of the skin or tubing to disconnect from the intravenous set. Use of a butterfly infusion set leaves a residual amount of radionuclide in the syringe, is cumbersome for one person, time consuming, may cause the needle to pop out of the skin or tubing to disconnect the intravenous set, due to the positive force of injection, makes a leak possible when changing syringes on the tubing, and no bolus or bolus flush is available without time delay in flow studies.

The principal object of the invention is to provide a multipurpose double barrel syringe which has great flexibility in administering two injectable materials through a single venipuncture.

An object of the invention is to provide a method of manufacture of a multipurpose double barrel syringe, which method has few and simple steps.

Another object of the invention is to provide a method of manufacture of a multipurpose double barrel syringe, which method is accomplished with facility, rapidity, ease and economy.

Still another object of the invention is to provide a method of manufacture of a multipurpose double barrel syringe, which method combines the component parts of two commercially available disposable hypodermic syringes and needles.

Yet another object of the invention is to provide a multipurpose double barrel syringe which is able to administer two individual injectable materials in rapid succession, using any desired volumes, through a single venipuncture.

Another object of the invention is to provide a multipurpose double barrel syringe which is easier to handle and has none of the disadvantages of known intravenous delivery systems.

Still another object of the invention is to provide a multipurpose double barrel syringe for use in a variety of dual radiopharmaceutical examinations in which only a single venipuncture is necessary when each cylinder of the syringe contains one of the radionuclides, which examinations include liver and lung imaging, dual-channel pancreatic imaging, dual-isotope method for diagnosis of intracardiac shunts and dual-isotope renal studies.

Yet another object of the invention is to provide a multipurpose double barrel syringe for accomplishing a bolus injection with an instantaneous saline flush. It is essential that a compact bolus be delivered into the vascular compartment when performing dynamic flow studies. Although, a spectrum of techniques have been adopted, all agree that expedient administration is a necessity. Rapid delivery may be facilitated when a bolus injection is immediately followed with a saline flush, especially when small volumes for injection are used. The double barrel syringe of the invention accomplishes this when the inner syringe contains the saline flush and the outer syringe the radiopharmaceutical of choice.

Another object of the invention is to provide a multipurpose double barrel syringe for introducing macroaggregated lung materials. When performing lung perfusion imaging studies, it is important to make a clean injection with little or no blood mixing with the particulate material, or radioactive emboli may form in the syringe. A variety of image artifacts have been documented in the literature due to intersyringe mixing of blood and particulate material. The double barrel syringe of the invention performs venipuncture so that blood enters only one compartment of the syringe and does not have an opportunity to mix with the particulate radiopharmaceutical in the other compartment.

Still another object of the invention is to provide a multipurpose double barrel syringe for following an injectable material with a flushing material, as frequently required in X-ray procedures, where dyes are rapidly injected and pictures taken.

Yet another object of the invention is to provide a multipurpose double barrel syringe for administering dual injections, via only one injection or skin puncture, while preventing the two drug contents of the two cylinders from being mixed prior to administration.

Another object of the invention is to provide a multipurpose double barrel syringe for performing an antagonistic test in which a strong drug is administered to bring on an attack or reaction in a patient for diagnosis of disease administering the antidote or neutralizing agent or drug immediately, via the second, or inner, syringe.

Still another object of the invention is to provide a multipurpose double barrel syringe for immediately administering an intravenous drug to a critically ill patient, with the outer cylinder containing an anticoagulant which keeps the passage to a vein open while the inner cylinder contains the emergency drug ready for introduction.

Yet another object of the invention is to provide a multipurpose double barrel syringe in any situation where the use of two syringes is indicated in a relationship where a two or three-way stopcock would be indicated.

Another object of the invention is to provide a multipurpose double barrel syringe whenever a material must be mixed with blood, and/or incubated, and reinjected into the patient such as, for example, in vitro labeling of red blood cells with $Tc^{99m}$. Any material is mixed under totally aseptic conditions, since there is cylinder-to-cylinder mixing without the use of a test tube or any peripheral volumetric containers or tubes.

Still another object of the invention is to provide a multipurpose double barrel syringe which functions as a wet-dry syringe for mixing prepackaged materials.

BRIEF SUMMARY OF THE INVENTION

In accordance with the invention, a method of manufacture of a multipurpose double barrel syringe from a first syringe having a first cylinder having a first predetermined capacity, a first hypodermic needle of a first gauge and a first piston plunger having a plunger tip with a smooth seating surface and a rear indentation and a second syringe having a second cylinder having a second predetermined capacity less than said first predetermined capacity, a second piston plunger and a second needle of a second gauge with a tip and a base, comprises the steps of disassembling the first and second syringes and retaining the first needle on the first cylinder and the second piston plunger in the second cylinder, inserting the second needle through the center of the plunger tip of the first piston plunger, cementing the second needle in the plunger tip of the first piston plunger, mounting the second needle and the plunger tip on the second cylinder to provide a second syringe assembly, and inserting the second syringe assembly in the first cylinder in a manner whereby the second syringe assembly functions as a second syringe and as a piston plunger assembly of the first cylinder.

The second needle is inserted in the plunger tip and cemented therein by inserting the second needle directly through the center of the plunger tip so that the needle tip thereof extends out of the smooth seating surface of the plunger tip, placing a few drops of contact adhesive into the rear indentation of the plunger tip, and pushing the second needle until the base thereof seats securely in the rear indentation.

The first syringe has a capacity of 5 ml and an 18 gauge first hypodermic needle.

The second syringe has a capacity of 3 ml and a 22 gauge second needle.

The second cylinder has a second collar extending substantially radially therefrom at one end thereof and the second piston plunger has a piston rod with a third collar extending substantially radially therefrom at one end thereof. The method further comprises the step of positioning a spacer member to extend between the second and third collars to prevent the second piston plunger from moving into the second cylinder except under manual pressure.

The method still further comprises the step of affixing a first end of the spacer member to the second collar and affixing a spaced opposite second end of the spacer member to the third collar.

In accordance with the invention, a multipurpose double barrel syringe comprises a first cylinder having a first predetermined capacity and a first hypodermic needle of a first gauge at a first end thereof, the first cylinder having a first collar extending substantially radially therefrom at a second end thereof spaced from and opposite the first end thereof. A second cylinder has a second predetermined capacity less than the first predetermined capacity. The second cylinder has a second collar extending substantially radially therefrom at a first end thereof and is slidably mounted in the first cylinder for movement in axial directions. A second piston plunger has a piston rod and a second plunger tip coaxially mounted at a first end thereof and is coaxially slidably mounted in the second cylinder for movement in axial directions. The piston rod has a third collar extending substantially radially therefrom at a second end thereof spaced from and opposite the first end thereof. A first plunger tip is coaxially mounted on a second end of the second cylinder spaced from and opposite the first end thereof and coaxially slidably movable with the second cylinder in the first cylinder in axial directions. A second needle of a second gauge extends coaxially through the axial center of the first plunger tip and is affixed to the first plunger tip whereby the second cylinder, the second plunger tip and the second needle provide a second syringe assembly functioning as a second syringe and, with the first plunger tip function as a piston plunger assembly of the first cylinder. The first cylinder, the first hypodermic needle and the first piston plunger assembly provide a first syringe assembly. A spacer member extends between the second and third collars for preventing the second piston plunger from moving into the second cylinder except under manual pressure.

The first plunger tip consists of rubber.

The first plunger tip has a smooth seating surface and a rear indentation. The second needle has a base seated securely in the rear indentation and a tip extending out of the smooth seating surface.

The spacer member comprises a rod of substantially rigid, but bendable, material.

The spacer member comprises a rod of substantially rigid, but bendable, material having a first end affixed to the second collar and a spaced opposite second end affixed to the third collar.

The spacer member comprises a bendable metal.

The first cylinder has a capacity of 5 ml and an 18 gauge first hypodermic needle.

The second cylinder has a capacity of 3 ml and a 22 gauge second needle.

BRIEF DESCRIPTION OF THE DRAWINGS

In order that the invention may be readily carried into effect, it will now be described with reference to the accompanying drawings, wherein:

FIG. 3 is a view of an embodiment of the multipurpose double barrel syringe of the invention;

FIG. 4 is a view of the embodiment of FIG. 3, with the second, or inner, cylinder fully depressed in the first, or outer, cylinder and the second, or inner, needle within the first, or outer, needle;

FIG. 5 is a view of the first and second needles of the embodiment of FIG. 3 showing the second needle moving into the first needle;

FIG. 10 is a view of the embodiment of FIG. 9, with the first cylinder being loaded with fluid from a fluid source;

FIG. 11 is a view of the embodiment of FIG. 3, with the first cylinder being discharged; and FIG. 12 is a view of the embodiment of FIG. 3, with the second cylinder being discharged, after the discharge of the first cylinder.

DETAILED DESCRIPTION OF THE INVENTION

Figure 1:
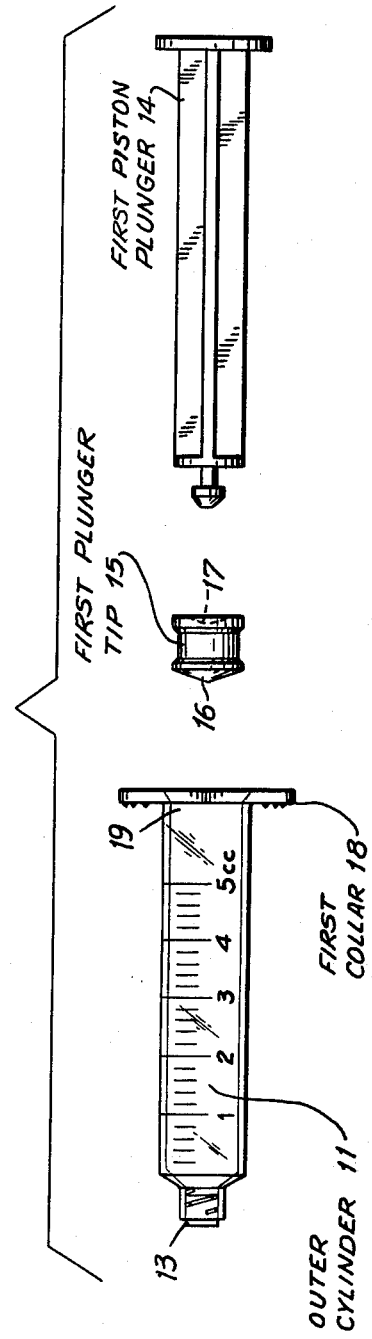
FIG. 1 is an exploded view of parts of a first hypodermic syringe, illustrating the first step of the method of the invention.

The multipurpose double barrel syringe of the invention is constructed from a 3 ml Luer syringe, manufactured by Becton-Dickinson Industries of Rutherford, N.J., having an attached 22 gauge 2½ inch hypodermic needle, No. 220 "Monoject" diamond point, manufactured by Sherwood Industries of St. Louis, Mo., and a 5 ml Luer syringe having an 18 gauge 1½ inch short bevel hypodermic needle, manufactured by Becton-Dickinson Industries and Sherwood Industries.

The 5 ml syringe is referred to herein as the first, or outer, syringe, and has a first, or outer, cylinder 11 (FIGS. 1, 3, 4 and 6 to 12) having a first capacity for 5 ml or 5 cc and a first, or outer, hypodermic needle 12 (FIGS. 3 to 6 and 9 to 12) of a first gauge or 18 at a first end 13 thereof (FIGS. 1, 3, 4 and 6 to 12). The first cylinder 11 has a first piston plunger 14 (FIG. 1) having a first plunger tip 15 (FIGS. 1, 2a, 2b, 2c and 3 to 12) with a smooth seating surface 16 (FIGS. 1, 2a, 2b and 2c) and a rear indentation 17 (FIGS. 1, 2a, 2b and 2c). The first cylinder 11 has a first collar 18 extending substantially radially therefrom (FIGS. 1, 3, 4 and 6 to 12) at a second end 19 thereof (FIGS. 1, 3, 4 and 6 to 12), spaced from and opposite the first end 13 thereof.

Figure 2C:
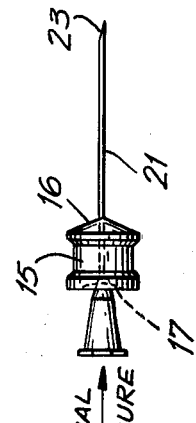
FIGS. 2a, 2b and 2c illustrate the second step of the method of the invention.
Figure 2B:
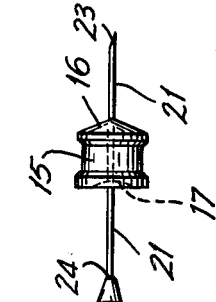
Figure 2A:
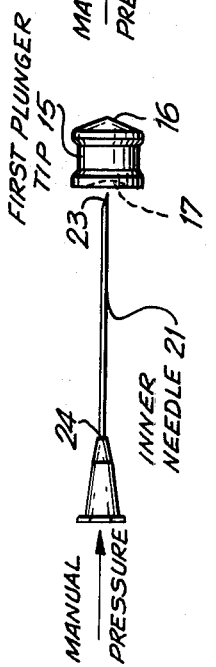

The 3 ml syringe is referred to herein as the second, or inner, syringe, and has a second, or inner, cylinder 20 (FIGS. 3, 4 and 6 to 12) having a second capacity of 3 ml or 3 cc, and a second, or inner, needle 21 (FIGS. 2a, 2b, 2c, 3 and 5 to 9) of a second gauge 22 with a tip 23 (FIGS. 2a, 2b and 2c) and a base 24 (FIGS. 2a and 2b). The inner cylinder 20 has a second piston plunger 25 (FIGS. 3, 4 and 6 to 12) and a second collar 26 extending radially therefrom (FIGS. 3, 4 and 6 to 12) at a first end 27 thereof (FIGS. 3, 4 and 6 to 12). The inner cylinder 20 is slidably mounted in the outer cylinder 11, as shown in FIGS. 3, 4 and 6 to 12, for movement in axial directions, indicated by arrows 28 and 29 (FIG. 3).

The second piston plunger 25 has a piston rod 30 (FIGS. 3, 4 and 6 to 12) and a second plunger tip 31 (FIGS. 3, 4 and 6 to 12) coaxially mounted at a first end 32 thereof (FIGS. 3 and 4). The piston rod 30 and second plunger tip 31 are coaxially slidably mounted in the outer cylinder 11 for movement in the axial directions 28 and 29, as shown in FIGS. 3, 4 and 6 to 12. The piston rod 30 has a third collar 33 extending substantially radially therefrom (FIGS. 3, 4 and 6 to 12) at a second end 34 thereof (FIGS. 3, 4 and 6 to 11), spaced from, and opposite, the first end 32 thereof.

The first plunger tip 15 is coaxially mounted on a second end 35 of the inner cylinder 20 (FIGS. 3, 4 and 6 to 12) spaced from, and opposite, the first end 27 thereof and is coaxially slidably movable with said inner cylinder in the outer cylinder 11 in axial directions 28 and 29, as shown in FIGS. 3, 4 and 6 to 12.

The inner needle 21 extends coaxially through the axial center of the first plunger tip 15 (FIGS. 2c, 3 and 5) and is affixed to said first plunger tip. The inner cylinder 20, the second plunger tip 31 and the inner needle 21 provide a second syringe assembly functioning as a second, or inner, syringe and, with the first plunger tip 34, functions as a piston plunger assembly of the outer cylinder 11.

The outer cylinder 11, the outer hypodermic needle 12 and the first piston plunger assembly provide a first syringe assembly.

The first plunger tip 15 preferably consists of rubber, although it may consist of any suitable pliable material. The base 24 of the second needle 21 is seated securely in the rear indentation 17 of the first plunger tip 15 and the tip 23 of said second needle extends out of the smooth seating surface 16 of said first plunger tip (FIG. 2c).

A spacer member 36 (FIGS. 3 and 8 to 12) extends between the second and third collars 26 and 33 and prevents the second piston plunger 25 from moving into the inner cylinder 20, as shown in FIGS. 3 and 8 to 11, except under manual pressure, applied by the user of the syringe, as shown in FIG. 12.

The spacer member 36 comprises a rod of substantially rigid, but bendable, material, such as, for example, a bendable metal, such as aluminum, copper, or the like. The rod 36 has a first end 37 affixed to the second collar 26 and a spaced opposite second end 38 affixed to the third collar 33, as shown in FIGS. 3 and 8 to 12, by any suitable means such as, for example, cement.

The spacer member 36 is positioned after the inner syringe has been filled with its proper contents, as hereinbefore described. When the inner cylinder 20 has been discharged, the spacer member bends or collapses under the pressure exerted manually by the user in accomplishing the discharge (FIG. 12).

If, in the absence of the spacer member 36, the outer cylinder 11 is loaded through the outer needle 12, there is a negative pressure created which tends to draw the contents of the inner cylinder 20 into said outer cylinder or into the vial being used to fill said outer cylinder. Secondly, if the spacer member 36 is not positioned when the outer needle 12 is in a vein, there is a negative pressure, or suction, exerted by the blood passing in the vein. This has a drawing effect on the inner needle 21 and subsequent contents of the inner cylinder 20. This causes a discharge of the inner cylinder 20 without pressing its plunger 25. When the outer needle 12 is in the vein, and the user draws back on the plunger of the outer cylinder 11, this effect of the unintended discharge of the inner cylinder 20 is greatly magnified. Furthermore, when the contents of the outer cylinder 11 are discharged, a positive pressure effect is created by resistance to the discharge. This causes a backup of the contents of the outer cylinder 11 which is attempting to discharge into the inner cylinder 20, which has not yet been discharged.

The spacer member 36 is initially cut or bent to a suitable length, as determined by the user, for its aforedescribed use.

The method of the invention, for manufacturing a multipurpose double barrel syringe involves the recombination of component parts of two commercially available disposable hypodermic syringes and needles, as hereinbefore mentioned. In the method of the invention, the aforedescribed commercially available first and second syringes are disassembled. The first, or outer, needle 12 is retained on the first, or outer, cylinder 11 and the second piston plunger 25 is retained in the second, or inner, cylinder 20. The first piston plunger 14 is discarded and the first plunger tip 15 is retained (FIG. 1).

In the method of the invention, the first plunger tip 15 is held firmly and the inner needle 21 is pushed directly through its center so that the needle tip 23 extends out of the smooth seating surface 16 of said plunger tip. A few drops of contact adhesive of any suitable type are placed in the rear indentation 17 of the plunger tip 15. The needle 21 is then pushed all the way, so that its base 24 seats securely in the plunger tip (FIG. 2).

The unit is set aside to dry for at least 6 hours. Once the cement is dry, the inner needle 21 and the plunger tip 15 are mounted on the inner cylinder 20 and this is then inserted into the outer cylinder 11, as shown in FIG. 3. The inner syringe and the inner needle 21 then perform the dual functions of a 3 ml syringe and of a piston plunger assembly for the outer cylinder 11 of the 5 ml syringe.

Each volumetric compartment of the double barrel syringe of the invention is separate, yet communication to the vein is afforded through the hypodermic needles 12 and 21. The inner 22 gauge needle 21 fits within the bore of the outer 18 gauge needle 12 when all of the piston units of the assembled syringe are seated (FIG. 4). The entire unit is then sterilized by radiation or gas. Once sterile, it is ready for use.

A combination of a 1 ml TB syringe with a 22 gauge 2½ inch hypodermic needle and a 3 ml syringe with an 18 gauge 1½ inch hypodermic needle can be used when smaller volumes for injection are desired.

Each syringe compartment must be loaded individually to its desired volume, following standard aseptic technique. The first to be loaded in each instance is the inner 3 ml cylinder 20. Standard loading procedure always begins with all the piston plunger assemblies seated and depressed.

Figure 6:
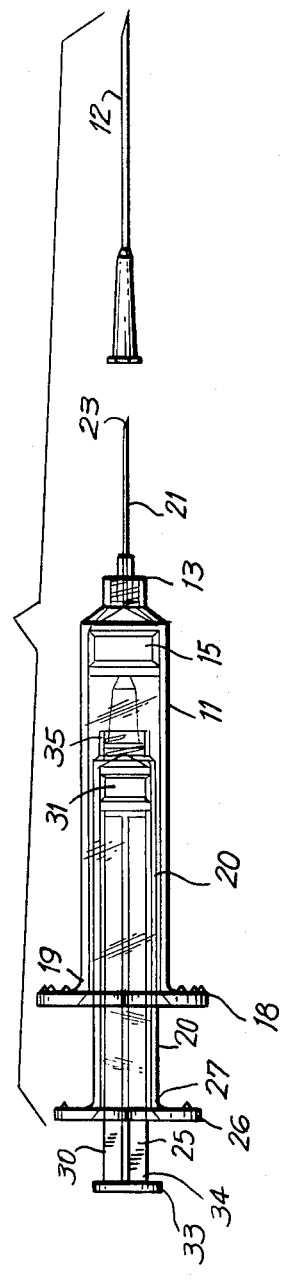
FIG. 6 is a view of the embodiment of FIG. 3, with the first needle removed from the double barrel syringe to enable loading of the second cylinder.

The inner cylinder 20 is loaded by removing the outer 18 gauge needle 12 from the 5 ml syringe. This exposes 2 inches of the inner 22 gauge needle 21 through which access and loading of the 3 ml inner cylinder is possible (FIG. 6).

Figure 7:
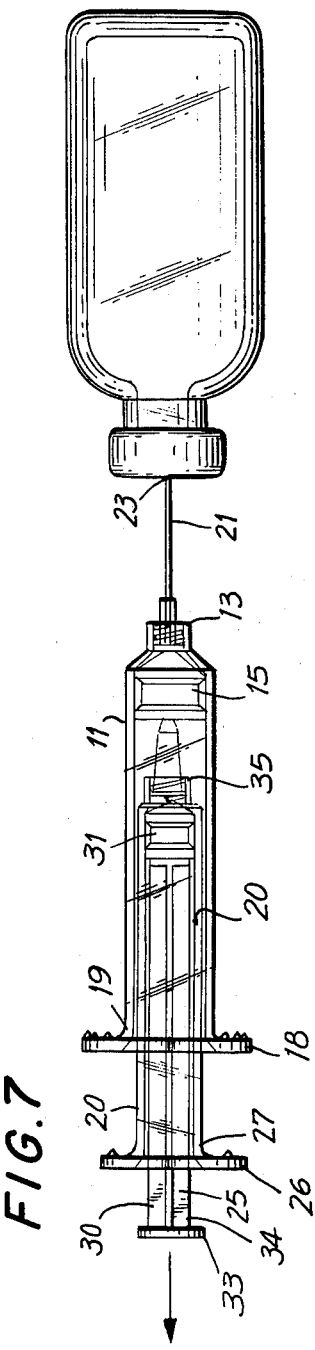
FIG. 7 is a view of the embodiment of FIG. 3, with the second cylinder being loaded with fluid from a fluid source.

Using the exposed tip 23 of the 22 gauge inner needle 21 and the standard plunger 25 of the 3 ml syringe, the 3 ml inner cylinder 20 is loaded to its desired volume (FIG. 7).

The spacer rod 36 is then positioned (FIGS. 8 to 12).

Figure 8:
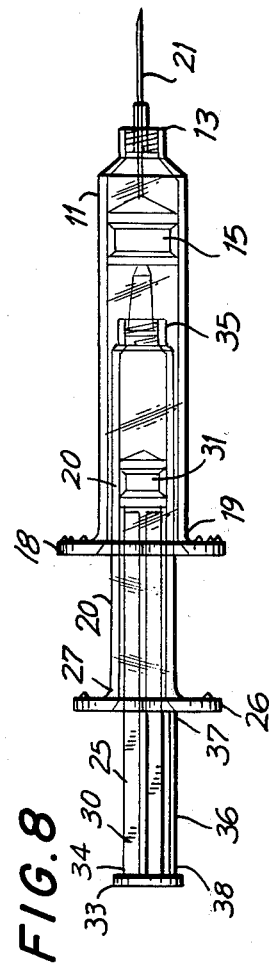
FIG. 8 is a view of the embodiment of FIG. 3, with the first needle removed and the second needle retracted to prepare for loading of the first cylinder.

The outer 5 ml cylinder 11 is loaded by drawing back on the inner cylinder 20 of the 3 ml syringe, which then functions as the piston assembly of said outer cylinder. This is done to retract the 22 gauge inner needle 21 into the outer cylinder 11 of the 5 ml syringe (FIG. 8).

Figure 9:
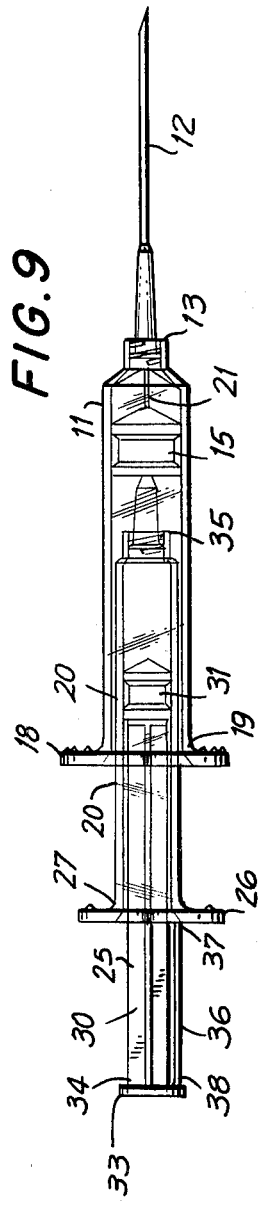
FIG. 9 is a view of the embodiment of FIG. 3, with the first needle restored and the second needle retracted.

The 18 gauge outer needle 12 is replaced on the outer cylinder 11 of the 5 ml syringe. When the inner cylinder 20 of the 3 ml syringe is depressed, the 22 gauge inner needle 21 will fit in the bore of the 18 gauge outer needle 12 (FIG. 9).

The 5 ml outer syringe is loaded following aseptic technique by drawing back on the inner cylinder 20 of the 3 ml syringe, which then functions as the piston assembly of the outer cylinder 11 (FIG. 10).

In loading the double barrel syringe of the invention, whichever material is to be injected first must be loaded in the outer cylinder 11 of the 5 ml syringe, and the second material to be injected must be loaded in the inner cylinder 20 of the 3 ml syringe.

The 22 gauge inner needle 21, the first plunger tip 15 and the 3 ml inner syringe then function as one unit controlling the volumetric capacity of the 5 ml outer cylinder 11. When the 3 ml inner syringe is pushed in, the first plunger tip 15 moves forward, rapidly discharging the contents of the 5 ml outer cylinder 11 directly through the 18 gauge outer needle 12 (FIG. 11).

The 3 ml inner cylinder 20 is discharged rapidly by pushing in on the piston 25 of the 3 ml inner syringe. The injected material then passes through the 22 gauge inner needle 21 to the 18 gauge outer needle 12, and into the lumen of the vein (FIG. 12). The manual force or pressure exerted by the user in pushing in the piston 25 bends the spacer member 36. Since the disposable multipurpose double barrel syringe has thus fulfilled its function, the bending of the spacer member 36 is of no import. The syringe is then discarded.

While the invention has been described by means of specific examples and in specific embodiments, I do not wish to be limited thereto, for obvious modifications will occur to those skilled in the art without departing from the spirit and scope of the invention.

I claim:

1. A method of manufacture of a multipurpose double barrel syringe from a first syringe having a first cylinder having a first predetermined capacity, a first hypodermic needle of a first gauge and a first piston plunger having a plunger tip with a smooth seating surface and a rear indentation and a second syringe having a second cylinder having a second predetermined capacity less than said first predetermined capacity, a second piston plunger and a second needle of a second gauge with a tip and a base, said method comprising the steps of disassembling the first and second syringes and retaining the first needle in the first cylinder and the second piston plunger in the second cylinder;

inserting the second needle through the center of the plunger tip of said first piston plunger;

cementing said second needle in said plunger tip of said first piston plunger;

mounting said second needle and said plunger tip on said second cylinder to provide a second syringe assembly; and inserting said second syringe assembly in said first cylinder in a manner whereby said second syringe assembly functions as a second syringe and as a piston plunger assembly of said first cylinder.

2. A method of manufacture as claimed in claim 1, wherein said second needle is inserted in said plunger tip and cemented therein by inserting said second needle directly through the center of said plunger tip so that the needle tip thereof extends out of the smooth seating surface of said plunger tip, placing a few drops of contact adhesive into the rear indentation of said plunger tip, and pushing said second needle until the base thereof seats securely in said rear indentation.

3. A method of manufacture as claimed in claim 1, wherein the second cylinder has a second collar extending substantially radially therefrom at an end thereof and the second piston plunger has a piston rod with a third collar extending substantially radially therefrom at an end thereof, and further comprising the step of positioning a spacer member to extend between said second and third collars to prevent said second piston plunger from moving into said second cylinder except under manual pressure.

4. A method of manufacture as claimed in claim 1, wherein said first syringe has a capacity of 5 ml and an 18 gauge first hypodermic needle.

5. A method of manufacture as claimed in claim 3, further comprising the step of affixing a first end of said spacer member to said second collar and affixing a spaced opposite second end of said spacer member to said third collar.

6. A method of manufacture as claimed in claim 4, wherein said second syringe has a capacity of 3 ml and a 22 gauge second needle.

7. A multipurpose double barrel syringe, comprising a first cylinder having a first predetermined capacity and a first hypodermic needle of a first gauge at a first end thereof, said first cylinder having a first collar extending substantially radially therefrom at a second end thereof spaced from and opposite said first end thereof;

a second cylinder having a second predetermined capacity less than the first predetermined capacity, said second cylinder having a second collar extending substantially radially therefrom at a first end thereof and being slidably mounted in said first cylinder for movement in axial directions;

a second piston plunger having a piston rod and a second plunger tip coaxially mounted at a first end thereof coaxially slidably mounted in said second cylinder for movement in axial directions, said piston rod having a third collar extending substantially radially therefrom at a second end thereof spaced from and opposite said first end thereof;

a first plunger tip coaxially mounted on a second end of said second cylinder spaced from and opposite said first end thereof and coaxially slidably movable with said second cylinder in said first cylinder in axial directions;

a second needle of a second gauge extending coaxially through the axial center of said first plunger tip and affixed to said first plunger tip whereby said second cylinder, said second plunger tip and said second needle provide a second syringe assembly functioning as a second syringe and, with said first plunger tip, functions as a piston plunger assembly of said first cylinder, said first cylinder, said first hypodermic needle and said first piston plunger assembly providing a first syringe assembly; and a spacer member extending between said second and third collars for preventing said second piston plunger from moving into said second cylinder except under manual pressure.

8. A multipurpose double barrel syringe as claimed in claim 7, wherein said first plunger tip consists of rubber.

9. A multipurpose double barrel syringe as claimed in claim 7, wherein said first plunger tip has a smooth seating surface and a rear indentation and said second needle has a base seated securely in said rear indentation and a tip extending out of said smooth seating surface.

10. A multipurpose double barrel syringe as claimed in claim 7, wherein said spacer member comprises a rod of substantially rigid, but bendable, material.

11. A multipurpose double barrel syringe as claimed in claim 7, wherein said spacer member comprises a rod of substantially rigid, but bendable, material having a first end affixed to said second collar and a spaced opposite second end affixed to said third collar.

12. A multipurpose double barrel syringe as claimed in claim 7, wherein said spacer member comprises a bendable metal.

13. A multipurpose double barrel syringe as claimed in claim 7, wherein said first cylinder has a capacity of 5 ml and an 18 gauge first hypodermic needle.

14. A multipurpose double barrel syringe as claimed in claim 13, wherein said second cylinder has a capacity of 3 ml and a 22 gauge second needle.

* * * * *